US012544567B2

(12) United States Patent
Clayman et al.

(10) Patent No.: US 12,544,567 B2
(45) Date of Patent: Feb. 10, 2026

(54) USE OF ELECTRICITY TO ENHANCE THE DELIVERY OF PHARMACEUTICAL AGENTS AND OTHER SUBSTANCES INTO THE SURFACE MUCOSA AND WALL OF THE URETER AND RENAL PELVIS, AND INTO THE RENAL PARENCHYMA

(71) Applicant: THE REGENTS OF THE UNIVERSITY OF CALIFORNIA, Oakland, CA (US)

(72) Inventors: Ralph V. Clayman, Orange, CA (US); Jamie Landman, Orange, CA (US); Seyed Hossein Hosseini Sharifi, Orange, CA (US); Pengbo Jiang, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 254 days.

(21) Appl. No.: 18/317,724

(22) Filed: May 15, 2023

(65) Prior Publication Data

US 2023/0364419 A1 Nov. 16, 2023

Related U.S. Application Data

(60) Provisional application No. 63/341,565, filed on May 13, 2022.

(51) Int. Cl.

*A61N 1/30* (2006.01)
*A61B 18/14* (2006.01)
*A61M 25/00* (2006.01)

(52) U.S. Cl.

CPC .......... *A61N 1/306* (2013.01); *A61B 18/1492* (2013.01); *A61M 25/0017* (2013.01); *A61M 2210/1082* (2013.01)

(58) Field of Classification Search

CPC .......... A61N 1/30; A61N 1/306; A61N 1/327; A61B 18/1492; A61B 5/6852;

(Continued)

(56) References Cited

U.S. PATENT DOCUMENTS 4,411,648 A * 10/1983 Davis ..................... A61N 1/306 604/21
5,486,160 A * 1/1996 Rossi ..................... A61N 1/306 607/40

(Continued)

FOREIGN PATENT DOCUMENTS

EP 0780139 A1 * 6/1997 ............... A61N 1/30
WO WO-2004064657 A2 * 8/2004 ......... A61B 18/1492

(Continued)

*Primary Examiner* — Wesley G Harris
(74) *Attorney, Agent, or Firm* — NGUYEN TARBET IP LAW

(57) ABSTRACT

A medical urology device for drug delivery to the lining and deeper tissues of the ureter and kidney. The present invention features an electromotive drug administration (EMDA) catheter device for deploying a fluid to deep tissues of a patient. The device includes a catheter body with fenestrations along its distal length. The device may further comprise a multiport component for allowing access to the catheter body. The device may further comprise a conductive wire removably disposed through the multiport component within the catheter body. Fluid may be directed through the multiport component and the plurality of fenestrations to the body structure of the patient. Electrical stimulation directed through the conductive wire enhances the penetration of medications with the same polarity to electrical stimulation into a body structure of the patient to allow the fluid to penetrate deep tissues.

18 Claims, 7 Drawing Sheets
(7 of 7 Drawing Sheet(s) Filed in Color)

(58) Field of Classification Search
CPC ...... A61M 2210/1082; A61M 25/1011; A61M 25/0017; A61M 31/00; A61M 2025/0004; A61M 2025/0681; A61M 25/0009; A61F 2002/048
See application file for complete search history.

(56) References Cited

U.S. PATENT DOCUMENTS

| | | | | | |
|---|---|---|---|---|---|
| 5,843,016 | A * | 12/1998 | Lugnani | A61N 1/306 604/21 |
| 6,923,805 | B1 * | 8/2005 | LaFontaine | A61N 1/40 606/41 |
| 11,839,761 | B2 * | 12/2023 | Hagness | A61K 48/0083 |
| 2005/0004516 | A1 * | 1/2005 | Vanney | A61B 18/1492 606/41 |
| 2009/0209950 | A1 * | 8/2009 | Starksen | A61B 17/0401 606/41 |
| 2014/0088585 | A1 * | 3/2014 | Hill | A61B 18/18 606/33 |
| 2016/0331450 | A1 * | 11/2016 | Ben-Ezra | A61M 19/00 |
| 2017/0021129 | A1 * | 1/2017 | Erbey, II | A61M 39/12 |
| 2017/0128639 | A1 * | 5/2017 | Erbey, II | A61M 1/80 |
| 2019/0099584 | A1 * | 4/2019 | Erbey, II | A61M 27/008 |

FOREIGN PATENT DOCUMENTS

| | | | | |
|---|---|---|---|---|
| WO | WO-2006127431 | * | 11/2006 | A61F 2/06 |
| WO | WO-2006127431 A2 | * | 11/2006 | A61B 17/00234 |

* cited by examiner

USE OF ELECTRICITY TO ENHANCE THE DELIVERY OF PHARMACEUTICAL AGENTS AND OTHER SUBSTANCES INTO THE SURFACE MUCOSA AND WALL OF THE URETER AND RENAL PELVIS, AND INTO THE RENAL PARENCHYMA

CROSS-REFERENCES TO RELATED APPLICATIONS

This application is a non-provisional and claims benefit of U.S. Provisional Application No. 63/341,565 filed May 13, 2022, the specification of which is incorporated herein in its entirety by reference.

FIELD OF THE INVENTION

The present invention is directed to a medical urology device for drug delivery to the lining and deeper tissues of the ureter and kidney.

BACKGROUND OF THE INVENTION

Kidney stones are one of the most common urologic conditions, with an estimated 1 in 10 adults affected by the disease. Efforts have been directed towards promoting the passage of kidney stones with pharmacologic therapies such as alpha-blockers and calcium channel blockers. For those stones that fail to pass and/or require minimally invasive surgical removal (i.e., ureteroscopy), the narrow caliber of the human ureter is the intrinsic limitation. Recent efforts have demonstrated that the placement of a ureteral stent for one week allows for a 30% increase in ureteral size. This increase in ureteral caliber allows for the placement of larger ureteral access sheaths, which in turn allows for more efficient stone removal. Ureteral stents, however, are not without their attendant costs and morbidities. A majority of patients experience stent colic, which can range from mild irritative symptoms to intractable pain requiring parenteral pain medications or premature removal of the ureteral stent.

Other studies have shown the beneficial effects of prescribing muscle relaxant medications for one week before the surgery to relax the ureter muscle, potentially precluding or decreasing the need for pre-stenting. A week of medical therapy has its own systemic side effects and indeed, there have been conflicting reports as to its efficacy. Some experts have tried acute intraluminal drug administration into the lumen of the ureter at the time of surgery; this approach has also met with limited success. The relative ineffectiveness of intraluminal drug administration is due to the relative impermeability of the ureteral lining. The permeability barriers include cellular layers and tight junctions. A glycosaminoglycan (GAG) layer consisting of a thick mucus layer of glycoproteins and proteoglycans lines the surface of the ureter's urothelial cells and acts as a barrier to penetration of any infused substances into the ureteral wall.

Pertinent to this patent application in addition to stone disease is urothelial carcinoma (UC). Urothelial carcinoma is the fourth most common cancer affecting predominantly the bladder. Nonetheless, up to 10% of all urothelial carcinomas affect the renal pelvis and/or ureter (i.e., upper tract transitional urothelial cancer [UTTUC]). More than 60% of UTTUCs are invasive at diagnosis, making it a far more aggressive disease than bladder UC. The incidence of UTTUC has risen over the last three decades by more than 50%. Due to the aggressive nature and high recurrence rate of UTTUC, radical nephroureterectomy—the complete removal of the affected kidney, ureter, and bladder cuff—remains the gold standard of treatment. Although radical nephroureterectomy yields a high recurrence-free rate and cancer-specific survival rate, it predisposes patients to chronic kidney disease and related cardiovascular morbidity. Thus, alternative treatment in the clinical management of UTTUC is important, especially treatments that would promote kidney-sparing. To address the current needs, a novel catheter was designed for continuous and site-specific chemotherapy delivery directly to the renal pelvis and calyces with electromotive drug administration (EMDA).

Earlier work in infusing chemotherapeutic drugs into the renal pelvis has been largely unsuccessful due to the short indwell time secondary to the rapid outflow of the infused material. In addition, as previously noted, the permeability barriers of the urothelial lining largely preclude any significant penetration of any infused chemotherapeutic agent.

EMDA is a technique used to enhance drug delivery deep into targeted tissues, such as the bladder. The application of intra-luminal low-power electrical current induces directional movement of charged molecules into the surrounding tissue surfaces. While EMDA in the bladder has been demonstrated to be safe and effective, its application in the ureter and renal pelvis has not been investigated, until studies completed in our laboratory. The renal pelvis and ureter are anatomically designed to rapidly propel urine from the kidney to the bladder; as such, maintaining renal pelvic or ureteral contact with an infused medication is challenging. This is further complicated by the urothelium and its attendant protective layer which blocks distribution of a drug into the deeper tissues of the renal pelvis or ureter.

The technique for initially employing ureteral EMDA (and more recently renal EMDA) is to improve a drug's penetration into the urothelial lining and the ureteral wall in order to acutely dilate the ureter during a stone removal procedure. Of note, no study has been published on the use of EMDA in the ureter and kidney. The present work has resulted in the development of a unique silver-wire-containing ureteral and renal pelvis EMDA catheter that can deliver drugs into the wall of the ureter when the silver wire is electrified.

In some embodiments, this catheter is able to apply EMDA throughout the renal pelvis and calyces. Applications of this catheter would be for amplifying penetrance of chemotherapeutic/immunomodulant, antibiotics, anti-inflammatory medications, medical treatment of stone disease (stone dissolution), muscle relaxants for inducing relaxation of the collecting system, etc., into the renal pelvis and calyces.

By using a newly designed catheter for application of EMDA in the renal pelvis, it would be possible to administer chemotherapeutic agents that would penetrate into the urothelial lining of the pelvis and calyces, thereby enhancing their effectiveness in both treating existent UTTUC and preventing its recurrence after endoscopic resection.

BRIEF SUMMARY OF THE INVENTION

It is an objective of the present invention to provide devices and methods that allow for electromotive drug administration (EMDA) in a catheter, as specified in the independent claims. Embodiments of the invention are given in the dependent claims. Embodiments of the present invention can be freely combined with each other if they are not mutually exclusive.

EMDA, as implied by the name, means the application of electrical current to enhance the penetrance of drugs into surrounding tissues.

In urology, it has been used to increase the penetration of chemotherapeutic agents to the bladder for the treatment of superficial bladder cancer. Drug delivery in this manner decreases the side effects of systemic administration while providing a high level of drug delivery to the targeted tissues.

By using a unique silver wire conductive catheter having a solid or spiral shape, the present invention implements EMDA to move drugs into the urothelium and the deeper layer of the ureter, renal pelvis, and renal parenchyma. This could result in rapid relaxation of the ureteral wall and thus enhance any procedure to remove kidney or ureteral stones that have become lodged in the ureter or are in the kidney, as a larger ureteral access sheath could be placed. The same setup could also be used for the delivery of other drugs to treat cancer (i.e. transitional cell cancer) of the lining of the ureter or kidney (renal pelvis and calyx), transitional cell cancer of the kidney, kidney infections, and/or inflammation.

Electromotive drug administration to the ureter may increase the penetration of instilled relaxing medications into and throughout the length of the ureter thereby providing for acute dilation of the ureter. This would allow for the passage of larger equipment for stone removals, such as larger ureteral access sheaths which would increase the safety and efficiency of stone removal from the ureter or kidney.

Current methods to increase ureteral caliber include oral pharmacologic agents, but this can have unintended systemic effects which limit their use as the drug needs to be administered for 5-7 days before the procedure. Also, the effectiveness of this approach remains highly controversial given negative results in some studies. Other methods include placing a ureteral stent for a week before the procedure; however, this increases patient morbidity and healthcare costs.

EMDA has the potential to increase the success rate of ureteroscopy for the removal of renal and ureteral stones in a more efficient and relatively inexpensive manner without incurring adverse systemic side effects.

In addition to ureteral dilation, other applications of EMDA in the ureter and pyelocaliceal system would allow for the delivery of chemotherapy agents for the treatment of upper tract urothelial carcinoma. This would avoid the usual systemic side effects that accompany both oral and parenteral chemotherapy. It would also avoid the need for hospital admission or observation given that there would be no systemic effect from the administered medication despite being able to achieve higher targeted tissue concentrations of the chemotherapeutic agent.

1. Inserting an EMDA nephrostomy tube and infusion of chemotherapeutic agents to treat upper tract transitional cell cancer.

2. Development of an EMDA renal delivery device in which the conducting portion of the silver wire is limited to a proximal coil. This could be used for the delivery of chemotherapeutic agents to treat transitional and possibly even renal parenchymal cancer. It could also be used to deliver a high dose of antibiotics into the renal parenchyma to treat pyelonephritis or a renal abscess.

Many medications are suitable for EMDA application (water soluble, small molecular weight, and positively or negatively charged molecules). EMDA has been used in different fields of medicine. In the bladder, it has been used effectively to treat bladder cancer, bladder pain syndrome, and overactive bladder, and for analgesia prior to endoscopic procedures. Bladder EMDA is provided via a pre-made bladder catheter with an internal coiled electrical wire to relay electrical current into the bladder, which then pushes drug within the infused fluid into the urothelium and into the wall of the bladder itself.

Drug delivery, in this manner, decreases the side effects associated with systemic administration while providing a high level of drug delivered into the targeted tissues. The upper urinary tract collecting system (renal pelvis and ureters) is anatomically designed to rapidly transfer urine from the kidney to the bladder which largely negates any impact of infused medications into the upper urinary tract.

There is no precedent for the use of EMDA in the ureter, renal pelvis or calyceal system. Previously, techniques for EMDA in the ureter developed in our laboratory, revealed that indeed a positively charged molecule (i.e. methylene blue) could be delivered beyond the urothelium and deeply into the wall of the ureter. Modifications that we have made to the ureteral EMDA catheter allowed for delivery of methylene blue specifically to the urothelium. Presently, the depth of penetration of the methylene blue into the submucosa of the renal pelvis and calyces and possibly into the parenchyma of the kidney is being assessed in our laboratory.

The present invention features an electromotive drug administration (EMDA) catheter device for deploying a fluid-born drug or other substance to deep tissues of the ureter, renal pelvis, and calyces (i.e. renal parenchyma) of a patient. In some embodiments, the device may comprise a catheter body. The catheter body may be hollow and have a plurality of fenestrations along a distal length of the catheter body where it is in contact with the area of interest. The device may further comprise a multiport component disposed at a proximal end of the catheter body with ports allowing access to the hollow interior of the catheter body. The multiport also provides connection to a central venous pressure line and enables the measurement of intraluminal pressure in order to maintain a low pressure in the renal pelvis and preclude any backflow of the infusion. The device may further comprise a conductive wire removably disposed through the multiport component within the catheter body. Fluid may be directed through the multiport component, through the catheter body, and through the plurality of fenestrations to the body structure of the patient. Electrical stimulation directed through the conductive wire may enhance the drug's penetration to the tissue and relax the muscles of the body structure (i.e., ureter) of the patient because it allows the fluid containing medication to penetrate deeper into the lining of the structure and into the wall of the structure.

The present invention features a method for deploying a fluid containing medication to deep tissues of a body structure of a patient and simultaneous application of electromotive drug administration (EDMA). In some embodiments, the method may comprise providing a catheter device as previously described. The method may further comprise positioning the catheter device at the body structure and directing electrical stimulation through the conductive wire. Electrical stimulation increases the penetration of medication to the tissue by applying the positive or negative charge (based on the medication's polarity) that repels a drug with the same charge from the conductive wire. The method may further comprise directing fluid through the multiport component such that it travels through the catheter body and the plurality of fenestrations to the body structure of the patient.

EMDA in the upper urinary tract would provide multiple benefits: the delivery of smooth muscle relaxants, the delivery of chemotherapeutic/immunomodulant agents for the treatment of UTTUC (upper tract transitional urothelial cancer), delivery of antibiotics in the case of renal infection, and providing anti-inflammatory agents to promote resolution of renal inflammation or promote healing after treatment of ureteropelvic junction obstruction. EMDA would avoid the usual systemic side effects that accompany both oral and parenteral administration of these medications. It would also avoid the need for hospital admission or observation, given that there would be no systemic adverse side effects from the administered medication while providing a higher targeted tissue concentration of the agent, thus providing for a more efficient, safer delivery of the medication. This could be a paradigm shift in the medical treatment of myriad maladies affecting the kidney.

One of the unique and inventive technical features of the present invention is the implementation of EMDA in a catheter suited for use in the ureter alone, in the renal pelvis/kidney alone or in both the ureter and kidney. Without wishing to limit the invention to any theory or mechanism, it is believed that the technical feature of the present invention advantageously provides for delivering medication to the deep tissues of the ureter and/or kidney by administration of EMDA. None of the presently known prior references or works have the unique technical features of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The patent application or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which.

Figure 5B:
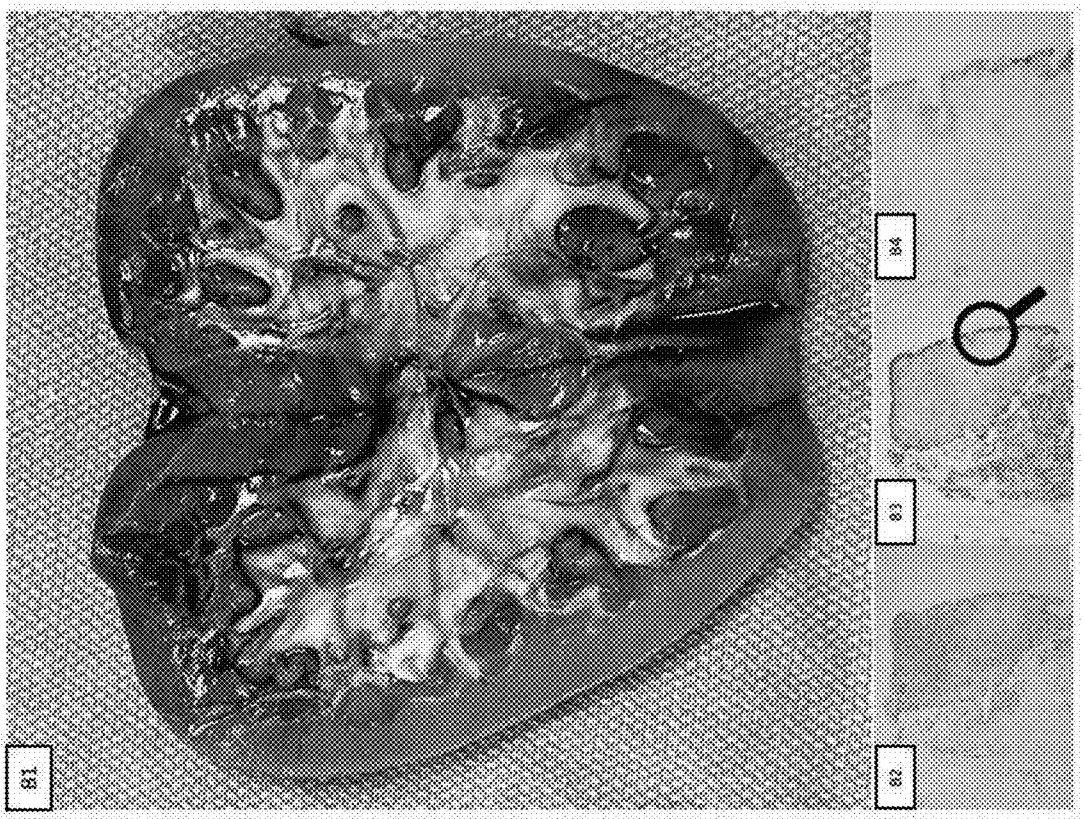
Figure 5A:
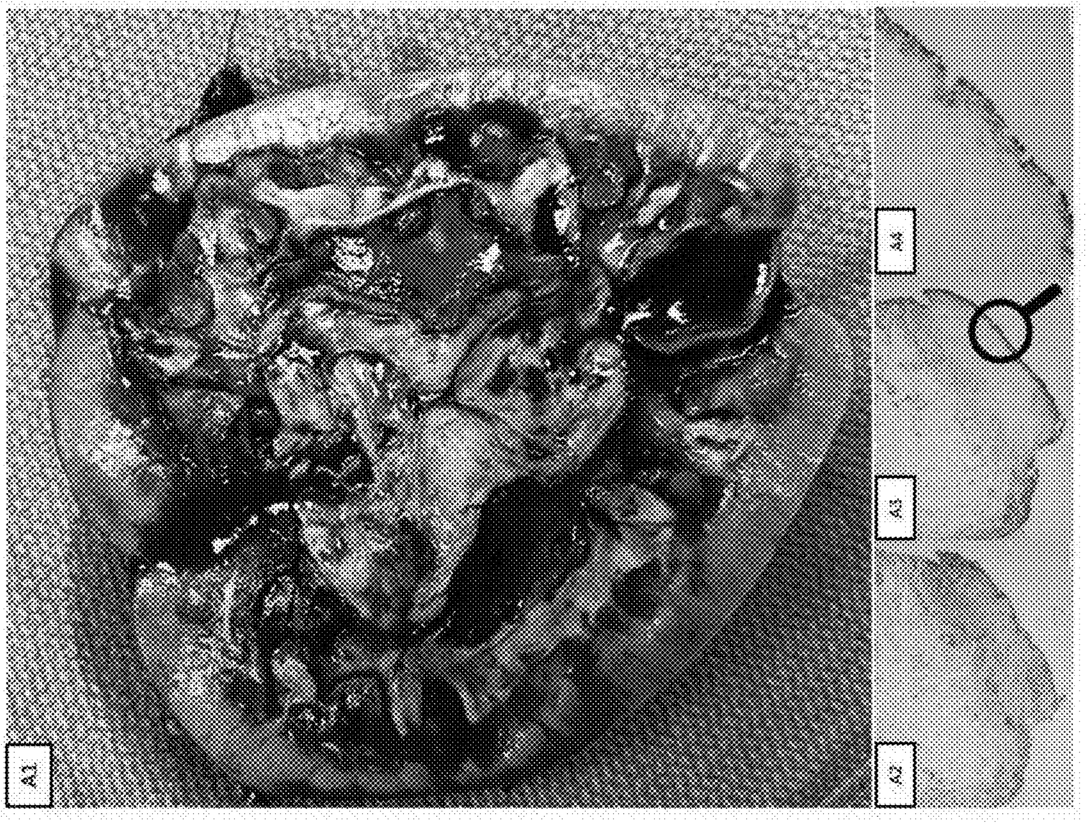

FIG. 5A shows a methylene blue infusion into the renal pelvis under the influence of EMDA: A1) Intense staining of the renal pelvis after the EMDA activation. A2) H&E staining shows a normal architecture with no signs of acute injury. A3&A4) Deep blue staining of urothelium and the submucosa of the renal pelvis.

FIG. 5B shows a methylene blue infusion of the renal pelvis without EMDA activation: B1) Faint staining of the renal pelvis after the infusion. B2) H&E staining shows a normal architecture with no evidence of injury. B3&B4) Blue staining of urothelium with less intensity and negligible methylene blue staining the submucosa of the renal pelvis.

DETAILED DESCRIPTION OF THE INVENTION

Figure 1A:
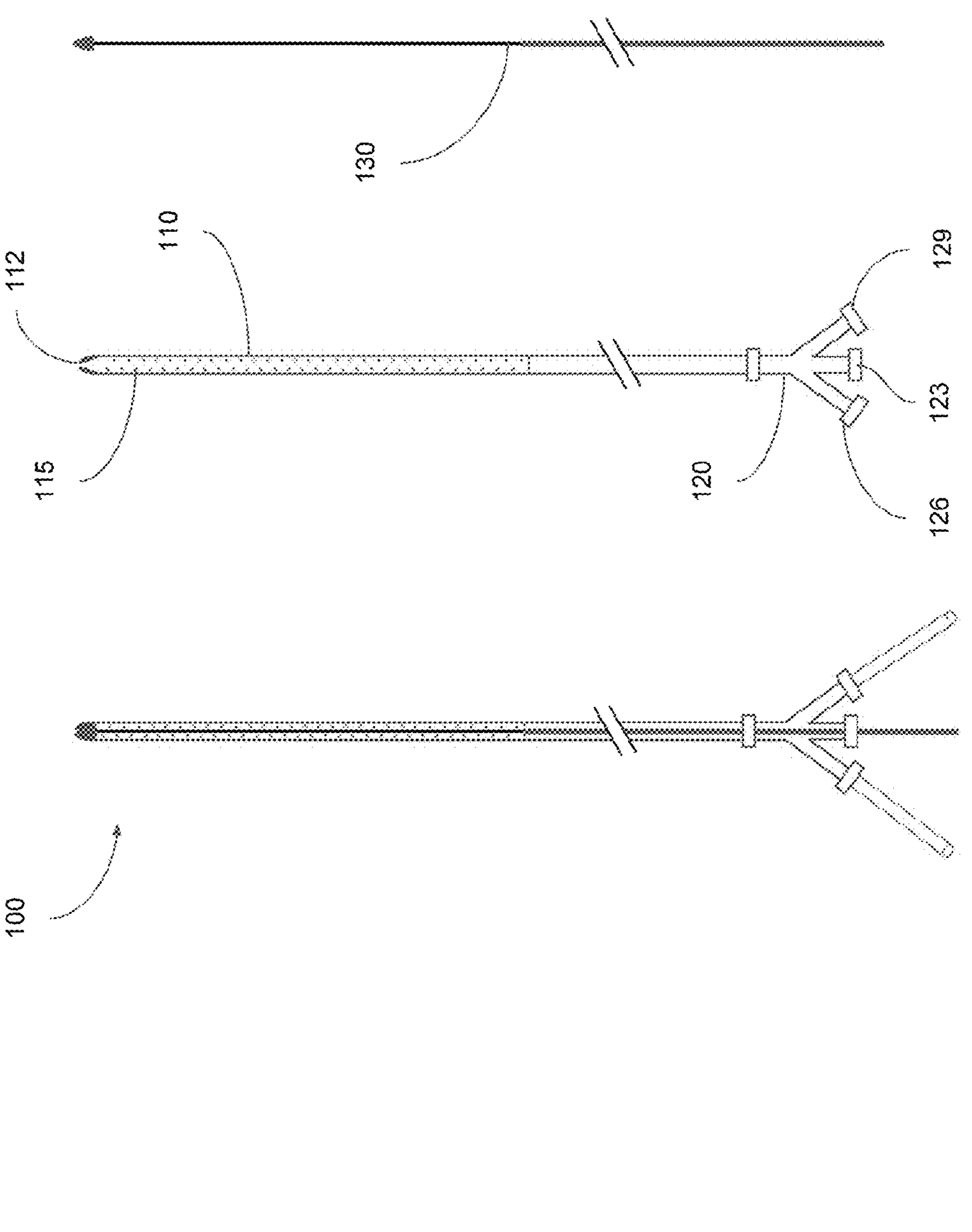
FIG. 1A shows a diagram of the EMDA catheter of the presently claimed invention suited for a ureter.
Figure 1B:
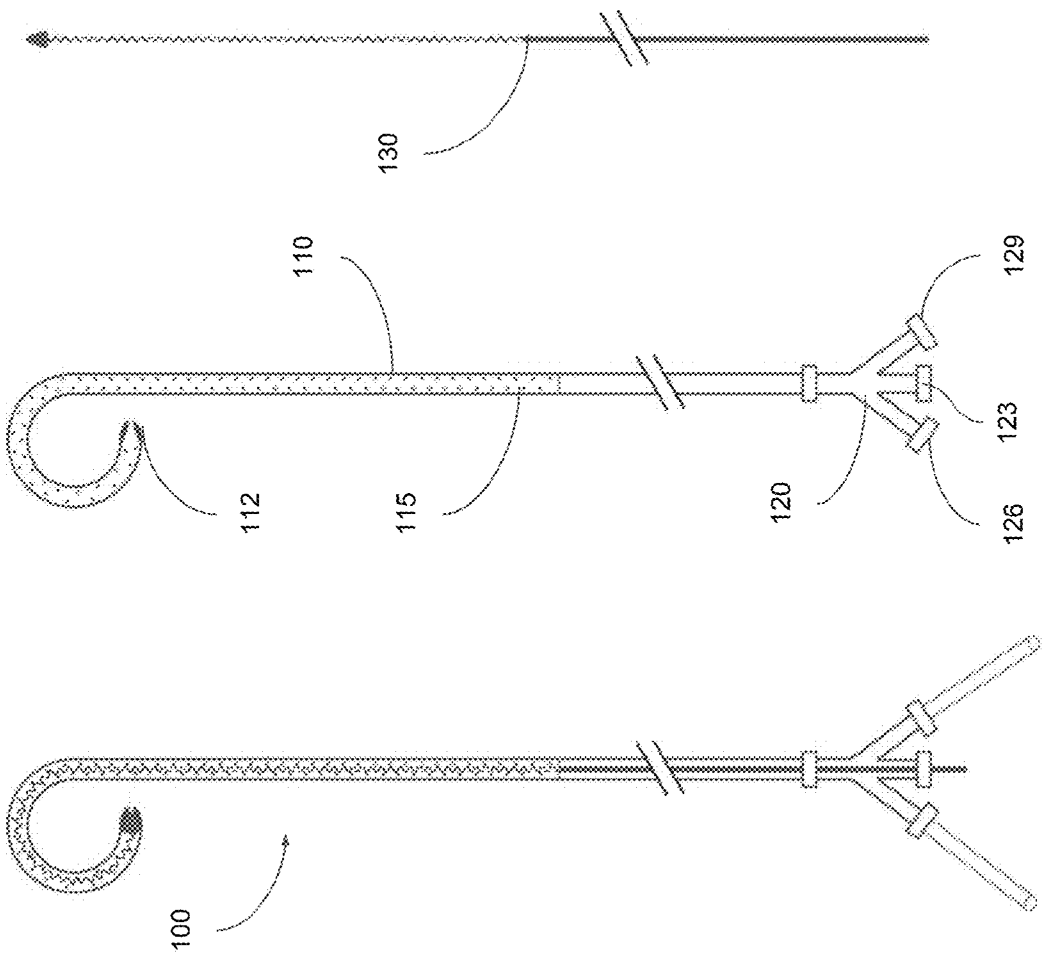
FIG. 1B shows a diagram of the EMDA catheter of the presently claimed invention suited for a renal pelvis.

Following is a list of elements corresponding to a particular element referred to herein:

100 device
110 catheter body
112 tip of catheter
115 fenestrations
120 multiport component
123 first port
126 second port
129 third port
130 conductive silver wire Referring now to FIGS. 1A-1B, the present invention features an electromotive drug administration (EMDA) catheter device (100) for amplifying the drug penetration into the deep tissues of a body structure of a patient. In some embodiments, the device (100) may comprise a catheter body (110) having a diameter of 3 to 20 Fr with a length of 30 to 80 cm. The catheter body (110) may comprise a hollow interior, and a plurality of fenestrations (115) disposed along a distal length of the catheter body (110). The device (100) may further comprise a multiport component (120) having a first port (123) and a second port (126) and a third port (129). The attachment (120) may be disposed at a proximal end of the catheter body (110). The first port (123) and the second port (126) may allow access to the hollow interior of the catheter body (110). The device (100) may further comprise a conductive wire (130) removably disposed through the first port (123) of the multiport component (120) within the hollow interior of the catheter body (110). Fluid may be directed through the second port (126) of the multiport component (120), through the catheter body (110), and through the plurality of fenestrations (115) to the body structure of the patient. Electrical stimulation directed through the conductive wire (130) may enhance the penetration of medication with positive or negative charge (same as electrical stimulation) and allow the fluid to penetrate deep tissues. In some embodiments, the catheter body (110) may have a straight end and may be suited for the ureter or kidney of a patient. In other embodiments, the catheter body (110) may have a curved end and may be suited for a renal pelvis and calyces of a patient.

Figure 2:
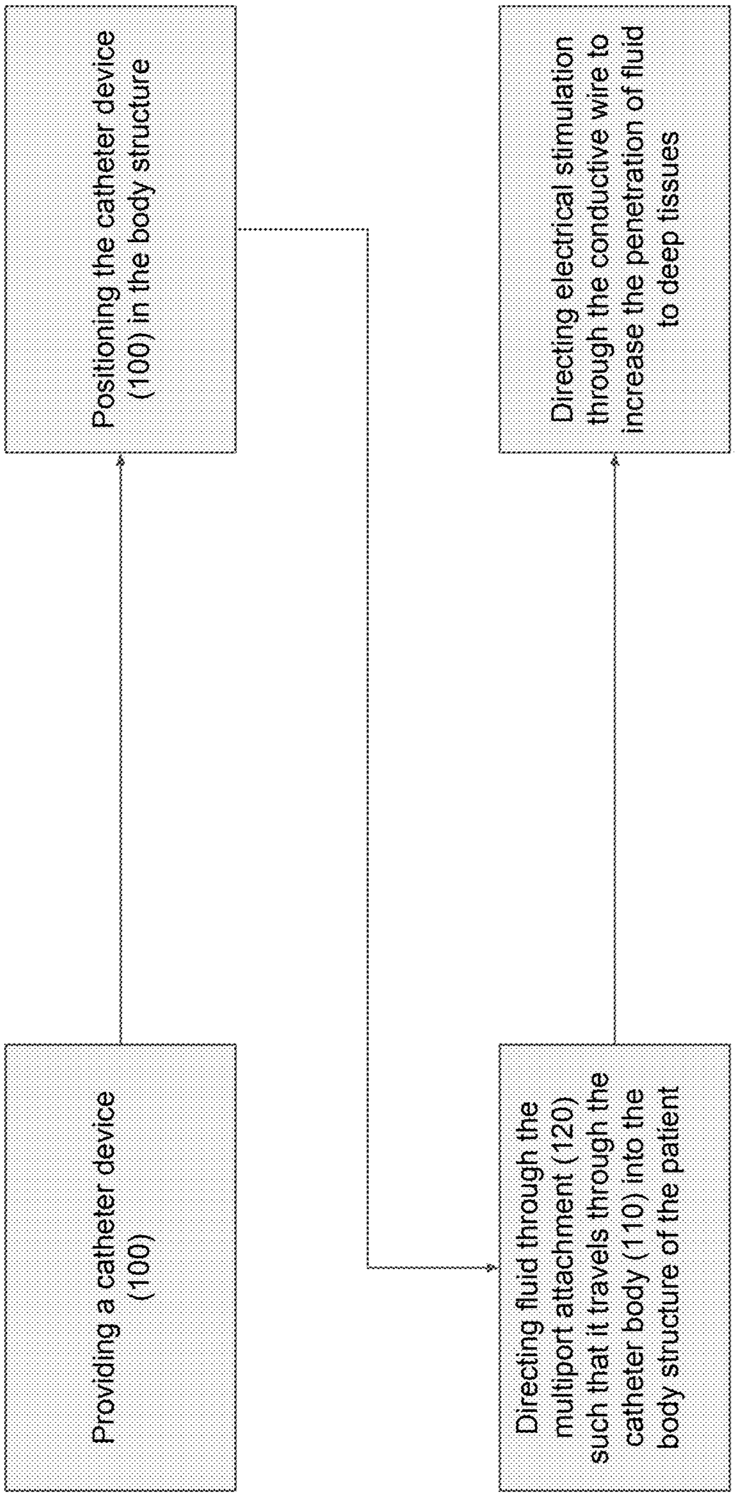
FIG. 2 shows a flow chart of the method for deploying a fluid to deep tissues of a body structure of a patient through electromotive drug administration of the present invention.

Referring now to FIG. 2, the present invention features a method for deploying a fluid to deep tissues of a body structure of a patient by application of electromotive drug administration (EDMA). In some embodiments, the method may comprise providing a catheter device (100). In some embodiments, the device (100) may comprise a catheter body (110) having a diameter of 3 to 20 Fr with a length of 30 to 80 cm The catheter body (110) may comprise a hollow interior and a plurality of fenestrations (115) disposed along a distal length of the catheter body (110). The device (100) may further comprise a multiport component (120) having a first port (123) and a second port (126) and third port (129). All these three ports can be used interchangeably. The attachment (120) may be disposed at a proximal end of the catheter body (110). The first port (123) and the second port (126) and third port (129) may allow access to the hollow interior of the catheter body (110). The device (100) may further comprise a conductive wire (130) removably disposed through the first port (123) of the multiport component (120) within the hollow interior of the catheter body (110). The method may further comprise positioning the catheter device (100) at the body structure and directing electrical stimulation through the conductive wire. The electrical stimulation increases the penetration of medications with the same electrical charge. The method may further comprise directing fluid through the ports (126) of the multiport component (120) such that it travels through the catheter body (110) but not out the tip of the catheter, thereby limiting the infusion fluid's distribution to only the ureter via the plurality of fenestrations (115) to the body structure (i.e., ureter) of the patient.

In some embodiments, the catheter body (110) may further comprise a hole (112) disposed at a distal end of the catheter body (110). Directing the device (100) into the body structure of the patient may comprise directing a distal end of a guidewire to the body structure of the patient, directing a proximal end of the guidewire through the hole (112) and the first port (123) of the device (100), moving the device (100) along the guidewire to the body structure of the patient, and removing the guidewire from the body structure and the device (100). The conductive wire may then be passed and with it being slightly larger than the tip of the catheter, it would plug the terminal hole in the tip of the catheter (112) to prevent the fluid from flowing through the tip of the catheter (112) thereby limiting the infusion only to those tissues exposed to the body of the catheter (e.g. to the ureter, but not to the renal pelvis and calyces).

In some embodiments, the multiport component (120) further comprises a third port (129) for measuring pressure. The pressure may be measured by a central venous pressure column or other internal or external means. The third port (129) may connect to a central venous pressure (CVP) line to measure the intraureteral pressure in order to prevent the adverse effect of high intraureteral pressure. In some embodiments, the CVP line may further attach to a higher-grade pressure measurement device. The CVP line may be used to keep the water pressure measured within the body at 40 cm or below. In some embodiments, the multiport component (120) may comprise any number of ports greater than two to provide for the dispensing of any number of separate fluids through the catheter device. In some embodiments, the multiport component (120) may be removably attached to the catheter body (110). In other embodiments, the catheter body (110) may be formed with the multiport component (120) attached.

The conductive wire (130) may comprise silver. The plurality of fenestrations (115) may be configured in two or more rows along the length of the catheter body (110). In some embodiments, the body structure may comprise a ureter, wherein the fluid comprises a relaxant to allow for acute dilation of the ureter. In other embodiments, the body structure may comprise a ureter or a kidney, wherein the fluid comprises medication for the treatment of infection, cancer, stone, or a combination thereof. In other embodiments, the catheter may be altered in length in order to provide for delivery of an infusion to the biliary tree or the intestines (e.g. esophagus, stomach, duodenum, small bowel, colon). In other more diminutive embodiments, the EMDA catheter could be used to deliver an infusion to smaller ductal structures (e.g. lacrimal ducts, salivary glands, etc.). In other embodiments the catheter could be modified to provide infusion delivery of a drug into a joint cavity to treat arthritis or inflammation.

A unique feature of the present invention is that it allows the application of EMDA for the first time for a wide range of ureteral and renal diseases, including stones, cancer, and infection. With EMDA, a wide variety of drugs could potentially be moved beyond the lining of the ureter and kidney into the depths of each of these tissues, providing for more effective, safer, and efficient drug delivery without incurring any systemic adverse side effects.

The EMDA delivery catheter designed and created in the laboratory has different lengths for use in female and male pigs, with a three-way luer-lock port proximally and a tapered distal end such that it can easily pass over a guidewire (i.e., 0.035 inch). In the distal 20 cm of the catheter, there are 0.3 mm fenestrations in three rows spaced equidistant (5 mm). Centrally, there is a silver wire to allow the conduction of electrical current. The silver wire may have a diameter such that when it is passed into the catheter it blocks the tip of the catheter. As such when fluid is infused into the catheter it can only come out the side holes that are in the lumen of the ureter. The catheter also precludes any direct contact of the electrified inner silver wire with the urothelium. Initial laboratory studies have shown no injury to the ureter or renal pelvis when the EMDA is used in this manner.

Cystoscopy is used to place a 0.035 in. guidewire into the ureter and up into the renal pelvis. The cystoscope is removed and the EMDA delivery catheter is advanced over the 0.035-inch super-stiff guidewire into the ureter up to the level of the ureteropelvic junction (i.e., not into the renal pelvis). A fluoroscopic image is obtained to confirm the correct position of the catheter in the ureter with the proximal tip just inside the renal pelvis. The 0.035 in. guidewire is removed and the silver wire is passed into the EMDA catheter. The circumference of the tip of silver wire (connected to positive electrode of EMDA generator) is larger than the exit hole in the distal tip of the EMDA catheter and thus its passage stops at the catheter's tip and occludes the end-hole, thereby preventing any flow of instilled fluid from the tip of the catheter. A dispersing electrode (negative) is placed on the flank area. The EMDA is then activated and the fluid containing the intended medication is instilled at 5 ml/min via a drug infusion pump for 20 minutes.

An electrical current of 10 mA is used to achieve a current density of less than 0.5 mA/cm$^2$. This value was obtained based on prior work in other areas with regard to the safety and efficacy of EMDA. The ureteral surface was multiplied [20 cm (length)×(circumference=1 cm)=20 cm$^2$] by 0.5 mA/cm$^2$. A pulsed or direct current can be used during EMDA.

Intra-ureteral pressure was measured by connecting the catheter to a CVP column designed to overflow if 40 cm of pressure is reached; this prevents any development of higher intrarenal pressure thereby precluding the possibility of any pyelo-venous/sinus/lymphatic backflow in the kidney. A 10 Fr Foley catheter is placed in the bladder for continuous urine drainage to maintain low intravesical pressure.

As proof of concept, a porcine study was performed (IACUC approved protocol: 21-131). A charged molecule, methylene blue, was instilled which is suitable for EMDA because of its net positive charge, small molecular size, and strong blue color. Via the EMDA catheter, a pulsed electrical current of 10 mA was applied for 20 minutes during instillation of the methylene blue solution The pigs were then euthanized and both ureters were harvested. Visually, the difference in the color density in the experimental (EMDA ureter) and control ureter (without EMDA) was apparent.

Histopathologic evaluation of harvested ureters after EMDA showed penetration of methylene blue throughout the wall of the EMDA treated ureter without any evidence of thermal damage to the ureter; the control ureter had minimal, patchy staining of the urothelial lining with negligible penetration of methylene blue beyond the urothelium.

The present invention allows the application of EMDA into the renal pelvis and calyces for the treatment of renal stones, UTTUC, inflammation, obstruction, and infection. With EMDA, a wide variety of drugs may potentially be moved beyond the lining of the renal pelvis and calyces into the depths of each of these tissues providing for more effective and efficient drug delivery.

The electrically insulated, EMDA renal pelvis delivery catheter maybe made in various lengths (35-55 cm), and various diameters (5-15 Fr), with a three-way luer-lock port proximally and a tapered distal end such that it can easily pass over a 0.035 in. guidewire. In some embodiments, in the distal 1-10 cm of the catheter, there are multiple 0.1 to 1 mm fenestrations in multiple rows spaced equidistant (1-10 mm) with no holes along the more distal shaft of the catheter in order to ensure delivery of the infused drug only to the renal pelvis. In other embodiments, the catheter would have the same fenestrations in the proximal and distal portion in order to deliver infused drug to both the renal pelvis and the ureter, which would be ideal in the case of UTTUC. The tip of the catheter may be flexible and upon withdrawal of the guidewire would form a "C" in order to conform to the shape of the renal pelvis. The silver wire is sufficiently pliable that its advance to the tip of the catheter would still preserve the "C" shape of the catheter. The pliable silver wire having a solid or spiral shape is placed in order to conduct the electrical current; the wire is slightly larger at its tip than the 0.035 inch guidewire over which the catheter has been passed; as such, the silver wire's tip is too large to exit the catheter thereby precluding the possibility that any bare wire would enter the renal pelvis or calyces.

In some embodiments, the catheter might remain straight such that it could be directed into a specific calyx via an infundibulum in order to deliver drug directly to a calyx of interest (e.g. a calyx that is the sole site of UTTUC).

Catheters could be assembled pre-operatively or made separately and assembled during surgery or produced as a single, sterile one time use item. The EMDA catheter could be made in a single or multi-channel depending upon how the physician wished to instill and drain the medication or even consider passing more than one conducting silver wire. Alternatively, a catheter for treatment of just a calyceal lesion could be designed by keeping the catheter straight as with the ureteral EMDA catheter with infusion exit apertures only along the distal 2-3 cm of the catheter.

The catheter of the present invention may be suitable and/or shaped for insertion into any columnar structure (e.g. esophagus, duodenum, small bowel, large bowel, salivary gland ducts, lacrimal ducts, biliary ducts) for EMDA applications. In some embodiments, EMDA may be used to dissolve Randall's plaques or plugs in the Bellini ducts and preclude stone disease before it develops.

Example

The following is a non-limiting example of the present invention. It is to be understood that said example is not intended to limit the present invention in any way. Equivalents or substitutes are within the scope of the present invention.

Two Yorkshire pigs were placed under general anesthesia. Cystoscopy was used to place a 0.035 in. super-Stiff™ guidewire into each ureter. A prefabricated ureteral catheter with equidistant (5 mm) fenestrations in three rows was advanced into each ureter. A silver wire was then passed into each ureteral catheter; the circumference of the silver wire was larger than the terminal opening in the catheter such that its passage stopped at the catheter's tip, thereby preventing any flow of instilled fluid from the tip of the catheter. Methylene blue, a heterocyclic aromatic dye with a net positive charge, was infused through each catheter at a rate of 5 ml/min. In the experimental ureter, a positive pulsed electrical current of 10 mA was applied using a Physionizer® EDMA device. After 20 mins, both ureters were harvested and flash-frozen for histopathological analysis.

Figure 3B:
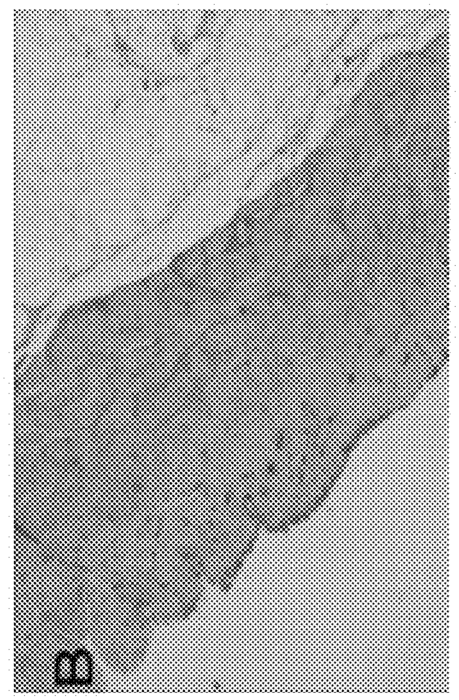
FIGS. 3B and 3C show normal architectures of the ureters in histopathologic evaluation of specimens with and without EMDA respectively.
Figure 3C:
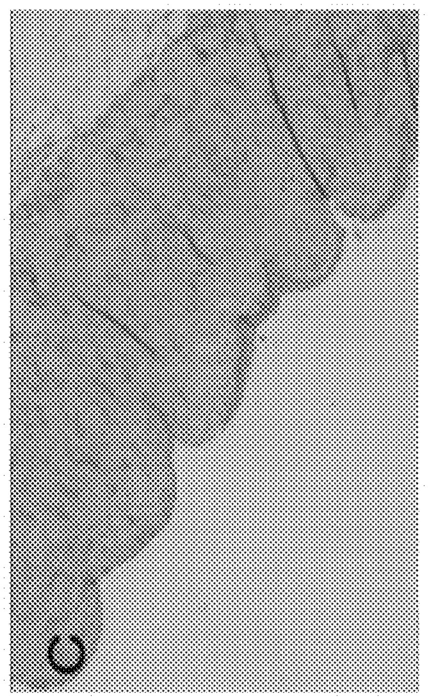
Figure 3A:
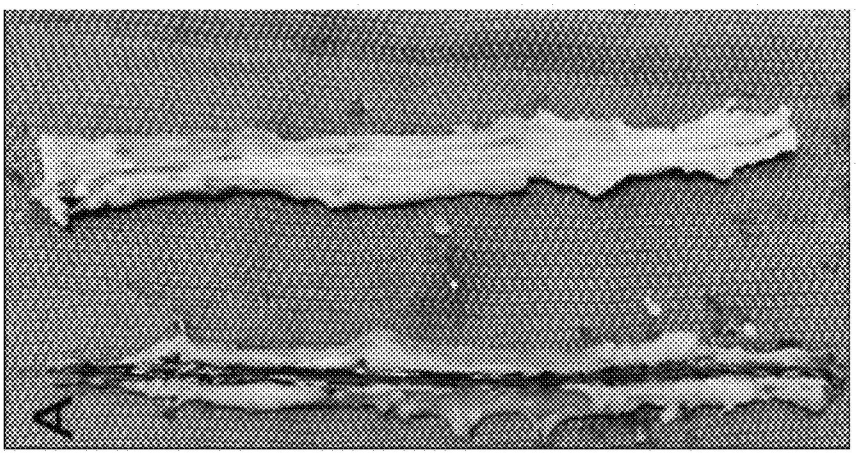
FIG. 3A shows an interior surface of ureters and intense staining of the experimental ureter after application of EMDA using fluid containing methylene blue (left side of the image) and minimal staining of the urothelial lining after instillation of methylene blue without EMDA (right side of the image).
Figure 3D:
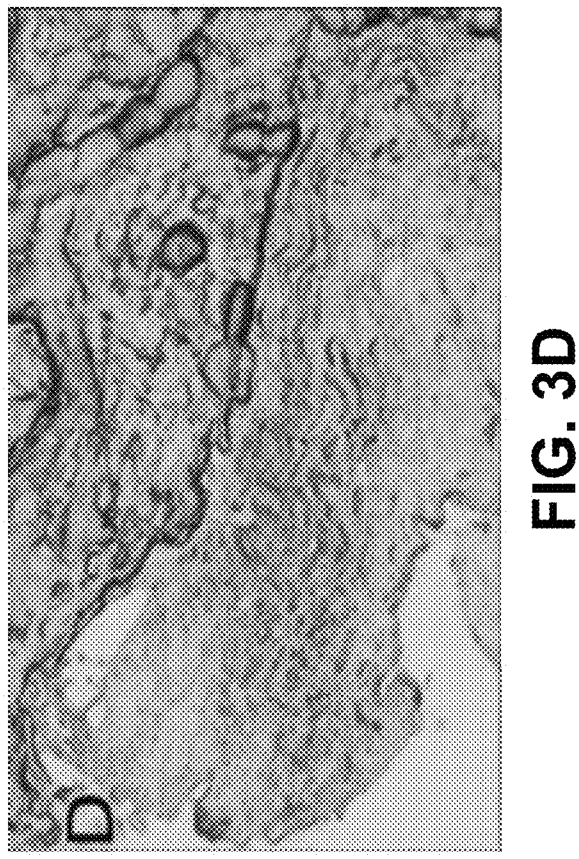
FIG. 3D shows the frozen section evaluation of ureter after application of EMDA using fluid containing methylene blue; note the dense blue staining of the urothelium.
Figure 3E:
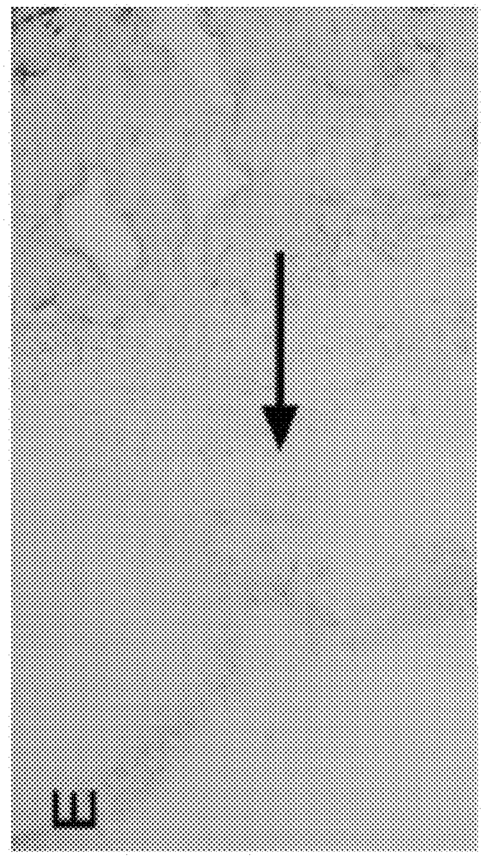
FIG. 3E shows frozen section evaluation of ureter without application of EMDA during infusion of fluid containing methylene blue; there is only patchy staining of the urothelium with methylene blue as pointed out by an arrow.
Figure 4:
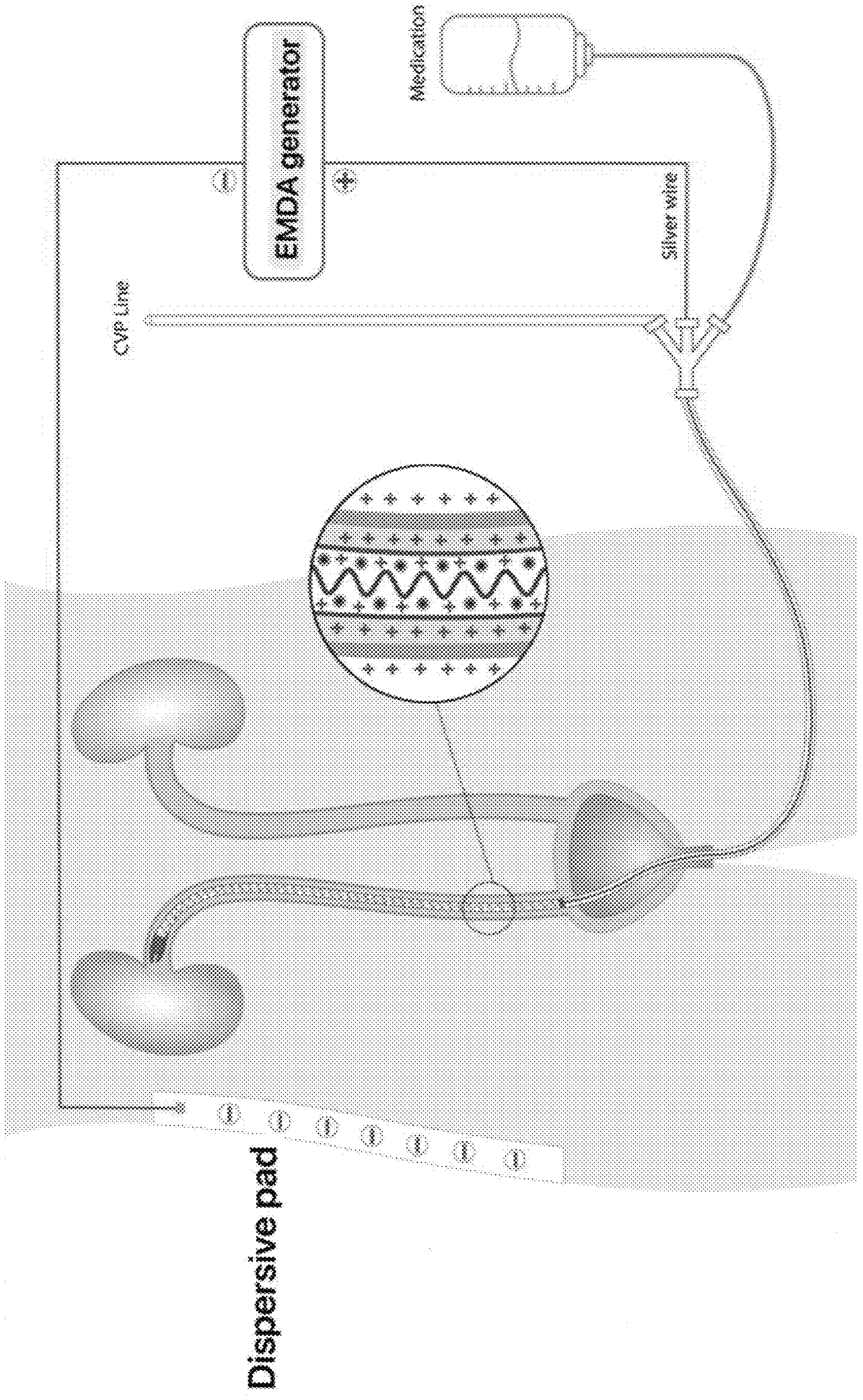
FIG. 4 shows a schematic image of the EMDA catheter of the present invention in use in a ureter. Silver conducting wire is connected to the positive electrode, and the dispersive pad is connected to the negative electrode.

Both animals tolerated the procedure well. Macroscopically, the difference in color density between the experimental and control ureter was apparent (FIG. 3A). Microscopically, in the experimental ureters, there was diffuse penetration of methylene blue into the urothelium, lamina propria, muscularis propria, and periureteral tissue (FIG. 3D). In the control ureter, patchy methylene blue staining was seen only on the urothelium with negligible deeper penetration (black arrows) (FIG. 3E). The experimental ureter showed mild urothelial cell denudation consistent with passage of the catheter; there was no sign of injury at the basal layer of the urothelium; the deeper tissues revealed no injury (FIG. 3B). EMDA at a current of 10 mA resulted in safe and successful penetration of methylene blue into all layers of the ureter and out to the periureteral soft tissue.

In another example, cystoscopy was used to place a 0.035 in. guidewire into the ureter and pass it up into the renal pelvis. The cystoscope is removed and a 5 to 15 Fr pigtail catheter is advanced over the guidewire; the guidewire is removed. A retrograde pyelogram is performed and the fluid is then drained from the renal pelvis and measured in order to obtain the volume of the renal pelvis. The guidewire is replaced and the pigtail catheter is removed and the EMDA delivery catheter is advanced over the guidewire into the ureter. A fluoroscopic image is obtained to confirm the correct position of the catheter with the proximal tip inside the renal pelvis. The guidewire is removed and the catheter assumes its nonintubated "C" shape along its proximal end; the silver wire is passed into the EMDA catheter (alternatively a pre-assembled catheter will be deployed via a preplaced ureteral access sheath) following the "C" shape of the distal end of the catheter. A solution containing the intended medication is instilled at a defined rate via a drug infusion pump for a defined time at a pressure no higher than 40 cm of $H_2O$ (the drug is contained in an infusion bag that is elevated above the patient to </=40 cm.) and the electrical current is then applied to the silver conducting wire throughout the drug infusion.

For renal pelvis EMDA, an electrical current of 4 mA (using a dedicated EMDA generator) is used in the C-shape catheter to achieve a current density of less than 0.5 mA/cm$^2$. This value is obtained based on prior work in the bladder with regard to the safety and efficacy of EMDA; the collecting system surface (8 cm$^2$) was multiplied by 0.5 mA/cm$^2$. A pulsed current is used during EMDA; however, direct current is also applicable.

Alternatively, intrarenal pressure is measured by connecting the catheter to a CVP column designed to overflow at 40 cm of water pressure; this prevents any excessive development of intrarenal pressure thereby precluding the possibility of any pyelovenous/sinus/lymphatic backflow. A 12F Foley catheter is placed in the bladder for continuous bladder drainage in order to maintain low intravesical pressure.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An electromotive drug administration (EMDA) catheter device (100) for deploying a fluid to deep tissues of a body structure of a patient, wherein the body structure comprises a ureter or a kidney, the device (100) comprising:

a. a catheter body (110) comprising:
   i. a hollow interior;
   ii. a hole (112) disposed at a distal end of the catheter body (110); and
   iii. a plurality of fenestrations (115) disposed along a distal length of the catheter body (110);

b. a multiport component (120) disposed at a proximal end of the catheter body (110), wherein the multiport component (120) comprises a first port (123) and a second port (126) configured to allow access to the hollow interior of the catheter body (110); and c. a conductive wire (130) removably disposed through the first port (123) and within the hollow interior of the catheter body (110), wherein a distal end of the conductive wire (130) is larger than the hole (112) so as to plug the hole (112) to prevent the fluid from flowing through the hole (112) and to prevent the conductive wire (130) from passing through the hole (112); wherein the device (100) is configured to have fluid directed through the second port (126), through the catheter body (110), and through the plurality of fenestrations (115) into the body structure of the patient; wherein the conductive wire (130), when exposed to electrical stimulation, is configured to repel molecules with similar polarity toward tissues and penetrate the body structure's lining and enter into a wall of the body structure.

2. The device (100) of claim 1, wherein the multiport component (120) further comprises a third port (129) for allowing access to the hollow interior for measuring pressure.

3. The device (100) of claim 1, wherein the conductive wire (130) comprises silver, copper, or any conductive material.

4. The device (100) of claim 1, wherein the plurality of fenestrations (115) is configured in two or more rows along the catheter body (110).

5. The device (100) of claim 1, wherein the fluid comprises a relaxant to cause dilation of the ureter to facilitate kidney stone removal.

6. The device (100) of claim 1, wherein the fluid comprises medication for treatment of infection, cancer, or a combination thereof.

7. The device (100) of claim 1, wherein the multiport component (120) is removably attached to the catheter body (110), or the catheter body (110) is formed with the multiport component (120) attached.

8. The device (100) of claim 1, wherein the catheter body (110) has a straight end or a curved end.

9. An electromotive drug administration (EMDA) catheter device (100) for deploying a fluid to deep tissues of a body structure of a patient, wherein the body structure comprises a ureter or a kidney, the device (100) comprising:

a. a catheter body (110) having a diameter of 3 to 20 Fr with a length of 30 to 80 cm comprising:
   i. a hollow interior;
   ii. a hole (112) disposed at a distal end of the catheter body (110); and
   iii. a plurality of fenestrations (115) disposed along a 20 to 55 cm distal length of the catheter body (110);

b. a multiport component (120) having a first port (123) and a second port (126), wherein the multiport component (120) is disposed at a proximal end of the catheter body (110), wherein the first port (123) and the second port (126) are configured to allow access to the hollow interior of the catheter body (110); and c. a conductive wire (130) removably disposed through the first port (123) of the multiport component (120) within the hollow interior of the catheter body (110), wherein a distal end of the conductive wire is configured to be larger than the hole (112) so as to plug the hole (112) to prevent fluid from flowing through the hole (112) and to prevent the conductive wire from passing through the hole (112);

wherein the device (100) is configured to have fluid directed through the second port (126) of the multiport component (120), through the catheter body (110), and through the plurality of fenestrations (115) to the body structure of the patient;

wherein the conductive wire (130), when exposed to electrical stimulation, is configured to repel molecules with similar polarity toward tissues and relax muscles of the body structure of the patient to allow the fluid to penetrate deep tissues.

10. A method for deploying a fluid to deep tissues of a body structure of a patient through electromotive drug administration (EMDA), wherein the body structure comprises a ureter or a kidney, the method comprising:

a. providing a catheter device (100) comprising:
   i. a catheter body (110) comprising:
      1. a hollow interior;
      2. a hole (112) disposed at a distal end of the catheter body (110); and
      3. a plurality of fenestrations (115) disposed along a distal length of the catheter body (110);
   ii. a multiport component (120) disposed at a proximal end of the catheter body (110), wherein the multiport component (120) comprises a first port (123) and a second port (126) configured to allow access to the hollow interior of the catheter body (110); and
   iii. a conductive wire (130) removably disposed through the first port (123) and within the hollow interior of the catheter body (110), wherein a distal end of the conductive wire (130) is designed to be larger than the hole (112) so as to plug the hole (112) to prevent the fluid from flowing through the hole (112) and to prevent the conductive wire (130) from passing through the hole (112);

b. positioning the catheter device (100) at the body structure;

c. directing fluid through the second port (126) of the multiport component (120) such that it travels through the catheter body (110) and the plurality of fenestrations (115) into the body structure of the patient; and d. directing electrical stimulation through the conductive wire, wherein the electrical stimulation allows the fluid to penetrate the deep tissues of the body structure.

11. The method of claim 10, wherein positioning the device (100) into the body structure comprises:

a. directing a guidewire to the body structure of the patient;

b. directing a proximal end of the guidewire through the hole (112) and the first port (123) of the device (100);

c. moving the device (100) along the guidewire to the body structure of the patient; and d. removing the guidewire from the body structure and the device (100).

12. The method of claim 10, wherein the multiport component (120) further comprises a third port (129) for allowing access to the hollow interior to measuring pressure, wherein the pressure is measured by a central venous pressure column.

13. The method of claim 10, wherein the conductive wire (130) comprises silver.

14. The method of claim 10, wherein the plurality of fenestrations (115) is configured in two or more rows along the distal length of the catheter body (110).

15. The method of claim 10, wherein the fluid comprises a relaxant to cause dilation of the ureter.

16. The method of claim 10, wherein the fluid comprises medication for treatment of infection, cancer, inflammation, stone disease, or a combination thereof.

17. The method of claim 10, wherein the multiport component (120) is removably attached to the catheter body (110), or the catheter body (110) is formed with the multiport component (120) attached.

18. The method of claim 10, wherein the catheter body (110) has a straight end or a curved end.

* * * * *